US006448066B1

(12) United States Patent
Wheatcroft

(10) Patent No.: US 6,448,066 B1
(45) Date of Patent: Sep. 10, 2002

(54) ROTARY THERMOCYCLING APPARATUS

(75) Inventor: Roger George Laurence Wheatcroft, Guelph (CA)

(73) Assignee: Her Majesty the Queen in right of Canada, as represented by the Minister of Agriculture and Agri-Food (CA)

( * ) Notice: Subject to any disclaimer, the term of this patent is extended or adjusted under 35 U.S.C. 154(b) by 0 days.

(21) Appl. No.: 09/876,428

(22) Filed: Jun. 6, 2001

Related U.S. Application Data

(63) Continuation of application No. PCT/CA99/01035, filed on Nov. 2, 1999.

(51) Int. Cl.$^7$ .................................................. C12M 1/34

(52) U.S. Cl. ................................ 435/287.2; 435/286.2; 435/287.3; 435/4; 435/91.1; 435/288.7; 422/64; 935/85

(58) Field of Search ........................... 435/287.2, 287.3, 435/286.2, 4, 91.1, 288.7, 303.1; 422/64, 82.05; 935/85

(56) References Cited

U.S. PATENT DOCUMENTS

| | | | | | |
|---|---|---|---|---|---|
| 4,683,202 | A | | 7/1987 | Mullis | 435/91 |
| 4,965,188 | A | | 10/1990 | Mullis et al. | 435/6 |
| 4,981,801 | A | * | 1/1991 | Suzuki et al. | 435/290 |
| 5,038,852 | A | | 8/1991 | Johnson et al. | 165/12 |
| 5,525,300 | A | | 6/1996 | Danssaert et al. | 422/99 |
| 5,723,294 | A | | 3/1998 | Glass et al. | 435/6 |
| 5,736,106 | A | * | 4/1998 | Ishiguro et al. | 422/131 |
| 5,779,981 | A | * | 7/1998 | Danssaert et al. | 422/99 |
| 6,197,572 | B1 | * | 3/2001 | Schneebeli | 435/286.2 |

FOREIGN PATENT DOCUMENTS

| | | | |
|---|---|---|---|
| DE | 196 46 115 A1 | 5/1998 | B01L/7/00 |
| EP | 0 438 883 A2 | 7/1991 | B01D/1/30 |
| EP | 0 723 812 A1 | 7/1996 | B01L/7/00 |
| WO | WO 94/08759 | 4/1994 | B25J/9/00 |
| WO | WO 94/21780 | 9/1994 | C12M/1/12 |

* cited by examiner

*Primary Examiner*—David A Redding
(74) *Attorney, Agent, or Firm*—Libert & Associates; Victor E. Libert

(57) ABSTRACT

A method for carrying out sequential reactions, e.g., sequential biochemical reactions, and a rotary thermocycling apparatus especially adapted for conducting such reactions, for example, polymerase chain reactions, are disclosed. The apparatus comprises a plurality of stations, e.g., four stations, for receiving biochemical samples in flat-bottomed containers. Heating means are provided to independently control the temperature of each station, transport means are provided to move the containers from one station to another in a predetermined sequence, and at least one station has a spray unit to spray liquid reagents into a container at that station. The method includes sequentially cycling a sample through predetermined temperature changes and spraying the sample with at least one reagent.

26 Claims, 4 Drawing Sheets

ROTARY THERMOCYCLING APPARATUS

This application is a continuation of International application No. PCT/CA 99/01035, filed Nov. 2, 1999, which is currently pending.

The present invention relates to a rotary thermocycling apparatus, and to methods of using rotary thermocycling apparatus, especially for use in biochemical reactions and in particular for use in polymerase chain reactions (PCR). In embodiments, the present invention is directed to rotary thermocycling processes in which samples are placed on filters, or other media, and heated on plates in a sequence at predetermined temperatures, preferably including at least one step in which the sample is sprayed e.g. with liquid reagent(s), during each cycle.

The present invention w ill be particularly described herein with respect to biochemical reactions.

It is frequently necessary or desirable to be able to quantify and/or detect the presence of certain nucleic acid molecules or microorganisms in samples of air, soils, water, food, body fluids and other materials. This may be necessary in relation to an immediate or health situation, or in testing to determine safety for use by humans or animals. Thus, in many instances, it is important to be Able to accurately and quickly confirm the presence and quantity of, or absence of, particular microorganisms in samples, and to do so in an automated, reliable and reproducible manner.

Traditional quantitative estimates of microorganisms in medical, food, environmental and other samples were based on colony counts after suitable culturing in diluted samples on nutrient agar plates. However, more accurate and rapid detection of microorganisms in various types of test samples has become possible.

Genetic information in al living organisms is carried largely in nucleic acids, either double-stranded deoxyribonucleic acids (DNA) or ribonucleic acid (RNA), and detection and discrimination on the basis of specific nucleic acid sequences has permitted the detection of the presence or absence of a particular organism within a test sample. The development of the polymerase chain reaction (PCR) process for amplifying one or more targeted nucleic acid sequences within a sample has greatly facilitated processes for detecting and discriminating specific nucleic acid sequences, and hence specific organisms.

PCR methods of detection require multiple or cyclic chemical reactions to produce a desired product, under carefully controlled temperature conditions to ensure accuracy and reproducibility, in order to produce sufficient material to enable detection of a microorganism in the sample, or indicate absence of the microorganism. Apparatus and methods have been developed which permit the accurate control of the temperature of reaction vessels in which such PCR amplification reactions may be performed. For example, there are a number of thermocyclers used for DNA amplification and sequencing in which one or more temperature controlled elements or "blocks" hold samples containing the reaction mixture, and the temperature of the block is varied over time. In other systems, a robotic arm is used to move mixtures from one block to another. These systems include features which allow the user to program temperatures or temperature profiles of the block over selected periods of time so that various processes e.g. DNA denaturing, annealing and extension, can be efficiently accomplished.

Polymerase chain reaction (PCR) is a technique involving multiple cycles that results in geometric amplification of certain polynucleotide sequences each time a cycle is completed. The technique is now well known. One example of PCR involves Denaturing a double-stranded polynucleotide, followed by annealing at least a pair of primer oligonucleotides to the resultant single-stranded polynucleotides. After the annealing step, an enzyme with polymerase activity catalyzes synthesis of a new polynucleotide strand that incorporates the primer oligonucleotide and uses the original denatured polynucleotide as a synthesis template to produce a new double-stranded polynucleotide molecule. This series of steps (denaturation, primer annealing, and primer extension) constitutes a PCR cycle. As cycles are repeated, the amount of newly synthesized polynucleotide increases geometrically because the newly synthesized polynucleotides from an earlier cycle can serve as templates or synthesis in subsequent cycles. Primer oligonucleotides are typically selected in pairs that can anneal to opposite strands of a given double-stranded polynucleotide sequence so that the region between the two annealing sites is amplified.

The temperature of the reaction mixture must be varied during each PCR cycle, and consequently varied many times during a test. For example, denaturation of DNA typically takes place at about 90°–100° C., annealing a primer to the denatured DNA is typically performed at about 40°–60° C., and the step of extending the annealed primers with a thermostable DNA-polymerase is typically performed at about 70°–75° C. Each of these steps may have an optimal temperature.

Examples of PCR are disclosed in U.S. Pat. No. 4,683,202, U.S. Pat. No. 4,965,188 and U.S. Pat. No. 5,038,852.

Apparatus in which a temperature gradient is generated across a gradient block is described in U.S. Pat. No. 5,525,300. Multiple reaction mixtures may be held in wells on the gradient block. In preferred embodiments, the gradient block is integrated into a thermocycler used for nucleic amplification reactions.

U.S. Pat. No. 4,981,801 describes an apparatus for carrying out enzymatic cycling reactions including a turntable, a number of reaction vessels arranged in the turntable around the periphery and means to circulate antifreeze liquid through the reaction tank. Heaters and refrigerators are provided in order to obtain variations in temperature.

An apparatus to detect and enumerate a particulate analyte in a liquid sample comprising a filter element in a holder and means to heat and control the temperature of the filter element, is disclosed in WO 94/21780 of R.G.L. Wheatcroft and W. B. Berndt.

A method for detection and discrimination of multiple analytes using fluorescent technology is disclosed in U.S. Pat. No. 5,723,294.

EP 0 723 812 describes a thermal cycling reaction apparatus having a reactor with a reactor body made of a thin heat conductive plate and having a cavity as reaction chamber.

Additional apparatus and methods for conducting thermocycling reactions, especially polymerase chain reactions, in a rapid automated and controlled mariner would be beneficial.

Accordingly, one aspect of the present invention provides rotary thermocycling apparatus, especially for biochemical reactions, comprising:

(a) a plurality of stations for receiving samples in a flat-bottomed container, each station having a flat heated plate on which said container is placed and having means to independently control said heated plate at a pre-determined temperature;

(b) means to move each said flat-bottomed container from one station to another station in a pre-determined sequence;

(c) at least two of said stations having a heating unit adapted to be lowered over a container located on said station, each heating unit being comprised of a section with a flat lower surface that is adapted to be lowered into said container close to but not in contact with the sample in said container; and (d) at least one station, in addition to the stations of (c), having a spray unit adapted to spray a liquid reagent(s) into a container located at said one station.

In a preferred embodiment of the invention, said station of (d) is adapted for removal of a cover plate from said container prior to activation of the spray, and for replacement of the cover plate after said spray has terminated.

In another embodiment, the container is a flat-bottomed container of a dimension less than that of t e station.

In a further embodiment, the heating is comprised of a section with a flat lower surface that is adapted to be lowered into said container close to but not in contact with the sample in said container, especially into contact with a cover plate therein.

In a still further embodiment, the apparatus has a programmer for controlling at least (i) the temperature at each station, (ii) the dwell time in each station, (iii) the duration and timing of the spray, (iv) the number of sequential cycles for the biochemical reaction.

In another embodiment, the container is adapted to receive a filter having the sample thereon, and to receive a cover plate over said filter.

In yet another embodiment, the apparatus is programmable and automated.

In a further embodiment it, the apparatus is adapted to process more than one sample at a time, up to one for each station in the apparatus.

In another embodiment, the heating units are on pistons that are lowered into the containers.

Another aspect of the present invention provides a method for a sequential reaction, especially a sequential biochemical reaction, at different temperatures, comprising:

(a) placing a sample in a flat-bottomed container;

(b) sequentially cycling said sample through predetermined changes in temperature by placing said flat-bottomed container on flat heated plate at each said temperature for a predetermined period of time;

(c) spraying said sample with at least one liquid reagent;

(d) controlling (i) the temperature at each station, (ii) the dwell time in each station, (iii) the duration and timing of the spray(s), and (iv) the number of sequential cycles for the biochemical reaction, said controlling of the temperature is at least two stations and includes the step of lowering a heating unit over the containers at said at least two stations, each heating unit being comprised of a section with a flat lower surface that is adapted to be lowered into said container close to but not in contact with the sample in said container.

In a preferred embodiment of the method of the invention, a biochemical sample is located on a filter, membrane, microtitre container or microscope slide in said container, especially a filter.

In another embodiment, the method is programmable and automated.

In a still further embodiment, the sample is subjected to a pretreatment prior to the method for the sequential reaction.

In a further embodiment, a spacer is placed on the filter and a cover plate is placed on the spacer.

In a further embodiment, the reaction is a polymerase chain reaction.

In another embodiment, the reaction is for detection of specific DNA sequences.

In a further embodiment, the sample is subsequently subjected to a photochemical detection process, especially fluorescence, to detect product of the reaction, and in particular to electronic recording thereof e.g. using a video camera.

A further aspect of the present invention provides rotary thermocycling apparatus especially for biochemical reactions, comprising:

(a) a plurality of stations for heating samples in a flat-bottomed container at predetermined temperatures;

(b) means to move each said flat-bottomed container from one station to another station in a pre-determined sequence; and (c) at least one station having a spray unit adapted to spray liquid reagent(s) into a container located at said one station.

Another aspect of the present invention provides a method for a sequential biochemical reaction at different temperatures, comprising placing a biochemical sample on a filter and sequentially cycling said biochemical sample through predetermined changes in temperature by heating said filter on a sequence of flat heated plates for a predetermined period of time.

A further aspect of the invention provides a method for a sequential biochemical reaction at different temperatures, comprising placing a biochemical sample on a filter and sequentially cycling said biochemical sample through predetermined changes in temperature, at least one step in the sequence involving spraying the sample with liquid reagent (s).

The present invention is illustrated by the embodiments shown in the drawings, in which.

The present invention is described herein with reference to a rotary thermocycling apparatus having four stations, each at a pre-determined temperature. This is the preferred number of stations, but is understood that the rotary thermocycling apparatus could have more or fewer than four stations at pre-determined temperatures, depending on the particular use intended for the apparatus. It is understood that, if there were more than four stations, more than one station, could have a spray unit.

For convenience, the container used in the apparatus will be generally referred to as a dish. However, other examples of containers are disclosed herein.

Figure 1:
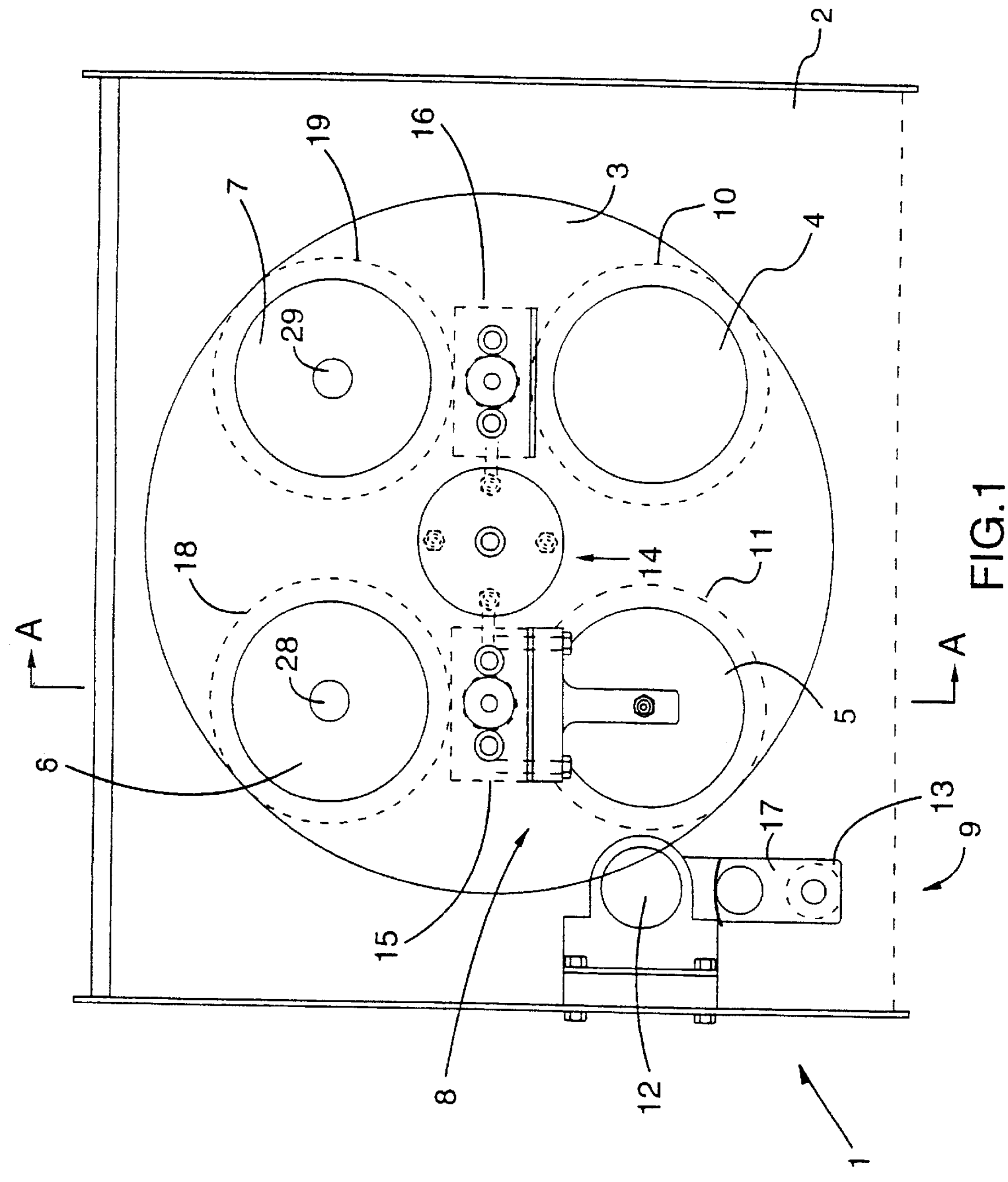
FIG. 1 is a schematic representation of a rotary thermocycling apparatus of the invention, in plan view.

FIG. 1 shows a rotary thermocycling apparatus, generally indicated by 1. Rotary thermocycling apparatus 1 has floor 2 on which is located rotating table 3. Rotating table 3 has four stations viz. first station 4, second station 5, third station 6 and fourth station 7. Rotary table 3 rotates about shaft. 14, so that a sample is moved in sequence from one station to the next. It is understood that the sample would be suitably located in a dish or other carrier receptacle, which would contact with the heated plate at each station.

Each location of the stations has a heated plate with each heated plate having means to independently control the temperature thereof at a predetermined temperature. The four stations are located symmetrically around rotating table 3 i.e. at 90° intervals. The heated plates are located at fixed locations in floor 2. First station 4 has heated plate 10, second station 5 has heated plate 11, third station 6 has heated plate 18 and fourth station 7 has heated plate 19. The heated plates do not rotate with rotary table 3, but rather rotary table 3 rotates so that each station is located over a heated plate when rotary table 3 is in each position of the sequence. Rotary table 3 does not rotate continuously, but moves in steps with a dwell time at each step.

First station 4 is an open station i.e. it is open for the placement of sample on the station, and does not have any spray or heating unit associated with it, as occurs for the other three stations, as discussed herein.

Second station 5 has spray unit 8 located above the station. Spray unit 8 is described in greater detail with respect to the subsequent drawings. Lid lifter 9 is located adjacent to second station 5. Lid lifter 9 has lid lifter shaft 17 which pivots about lid lifter pivot 12. The end of the lid lifter shaft 17 opposed to lid lifter pivot 12 has lid lifter suction cup 13 located thereon. Lid lifter 9 is adapted to rotate about lid lifter pivot 12 so that lid lifter suction cup 13 is located above second station 5. In addition, lid lifter 9 is adapted to move downwards towards second station 5. The operation of the lid lifter is discussed below.

Each of third station 6 and fourth station 7 has a heating unit associated therewith and which is lowered onto samples at these stations, as discussed herein. The heating units are not shown in FIG. 1 (see FIGS. 2 and 3), but are attached to supports 128 and 29, respectively.

Each of the four stations has a heated plate located at the position of the station, as discussed above that may be controlled at a predetermined temperature. The heated plate is most preferably heated using electrical heating. While the temperature of each of the stations may be varied over a wide range, and controlled at such temperature, a typical arrangement of temperature of the heated plates at the four stations is first station 50° C., second station 50° C., third station 72° C. and fourth station 96° C. Such temperatures are typical of temperatures for use with polymerase chain reactions, but the temperatures may be varied. The apparatus of the present invention preferably has suitable automated control systems, as discussed below.

Figure 2:
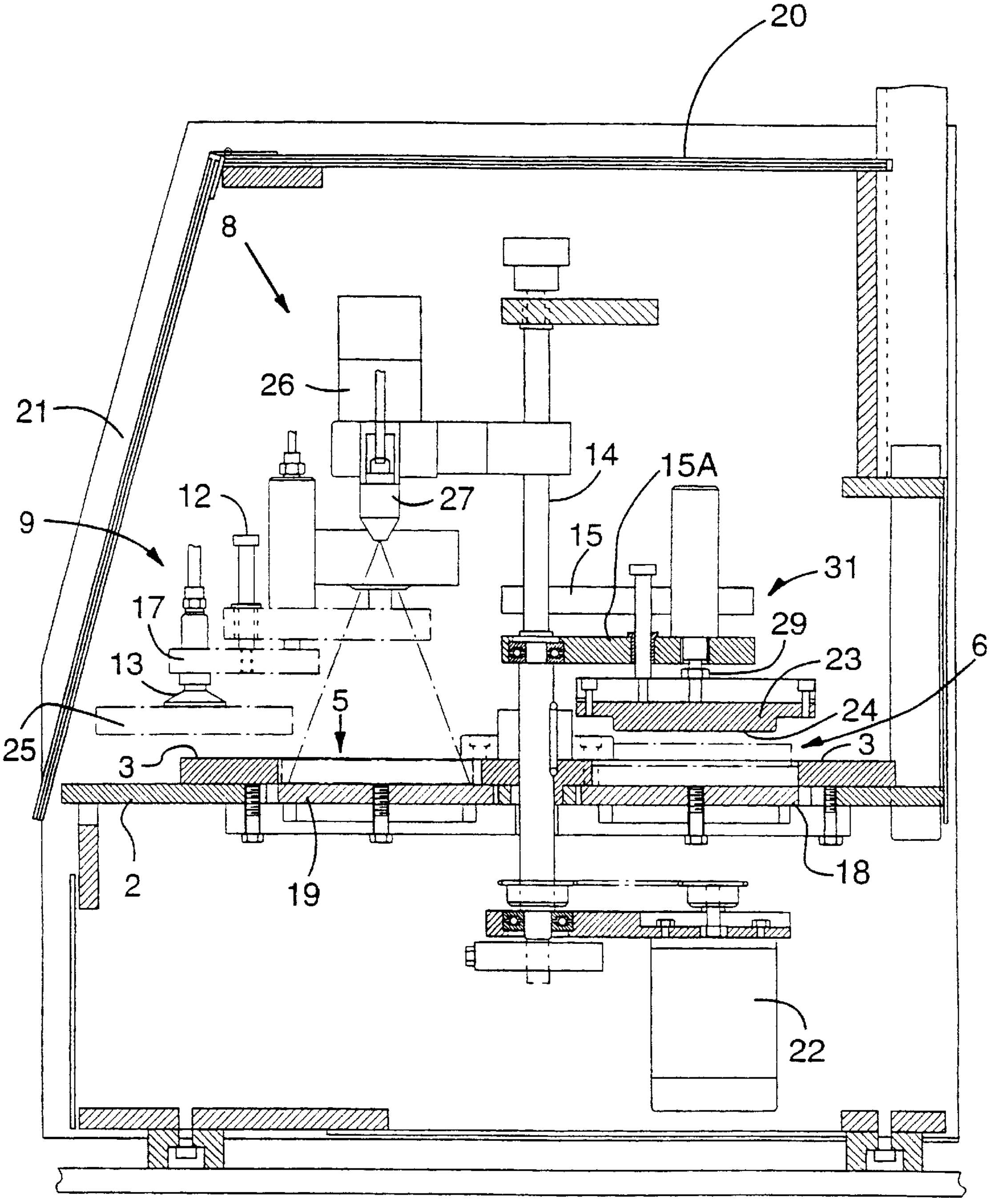
FIG. 2 is a schematic representation of the rotary thermocycling apparatus of FIG. 1, as seen through A—A.

FIG. 2 relates to the apparatus of FIG. 1, as seen through A—A. FIG. 2 shows rotary thermocycling apparatus 1 located within housing 20. Housing 20 has housing window 21 alone the front side of the apparatus, for viewing of the thermocycling apparatus in use. Housing 20 has floor 2 located away from the base of housing 20, primarily for the purpose of convenience and for location of motors and other operating parts of the thermocycling apparatus beneath floor 2. Shaft 14 extends upwards through floor 2 at a substantially central location, and is connected to drive motor 22 to effect rotation of shaft 14. Rotating table 3 is rotated by means of shaft 14. Shaft 14 could be adapted to provide support, with suitable bearings, for each of the heating units of the third and fourth stations, and for spray unit 8. However, the heating units would normally be attached to supports 15 and 16.

Second station 5 and third station 6 are shown as being located in rotating table 3. Spray unit is located above second station 5 and first heating unit 31 is located above third station 6. Second station 5 has heated plate 11, which is located in floor 2 and is not part of rotary table 3. Similarly, third station 6 has heated plate 18, also in floor 2 and not part of rotary table 3.

First heating unit 31 is shown in a partially lowered position, as represented by support 15 being in position 15A. First heating unit 31 has heating section 23 located on the underside thereof. It will be noted that heating section 23 is of a shape so that central region 24 of heating section 23 will enter into third station while the upper portion of heating section 23 extends beyond the circumference of third station 6. It is intended that heating section 23 would lower to a position such that central region 24 of heating section 23 would enter into third station 6. The purpose of central region 24 entering into third station 6 will be discussed below.

Second heating unit 32 is located above fourth station 7 in the same manner as first heating unit 31 is located above third station 6.

Spray unit 8 is located above second station 5. Spray unit 8 has lid lifter 9 associated therewith. Lid lifter 9 has lid lifter suction cup 13 connected, through lid lifter shaft 17, to lid lifter pivot 12. Lid lifter 9 is intended to rotate about pivot 112 so that suction cup 13 becomes located above second station 5. In addition, lid lifter 9 is then adapted to cause suction cup 13 to descend into second station 5 for the purpose of lifting a cover, 25 (see 64 in FIG. 5), from a sample dish located within second station 5, as discussed below. FIG. 2 shows cover 25 located on suction cup 13, but in a position disposed away from second station 5, to permit a spray from spray unit 8 to be sprayed onto a sample in second station 5.

Spray unit 8 may be of a variety of designs, but is shown in the form of a spray container 26 having a spray nozzle 27. In this embodiment, it is intended that spray container 26 would be an aerosol container or a pump action sprayer, or other type of spraying containing the required liquid reagent (s) to be sprayed onto the sample. A preferred embodiment of spray unit 8 is shown in FIG. 4.

Figure 3:
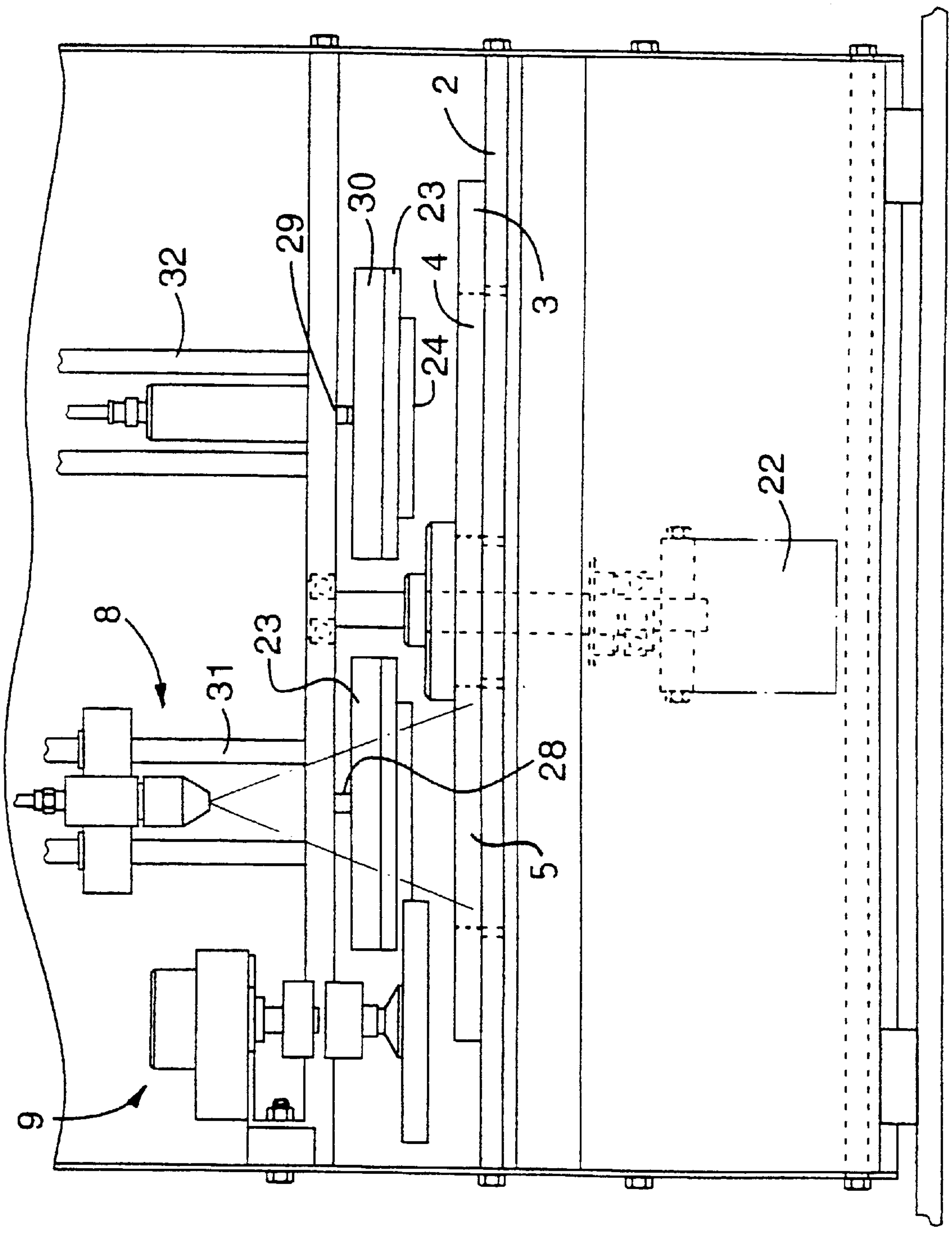
FIG. 3 is a schematic representation of a front view of the rotary thermocycling apparatus of FIG. 1.

FIG. 3 shows a front view of rotary thermocycling apparatus 1. This view shows first station 4 and second station 5, with first heating unit 31 of third station 6 located behind second station 5, and second heating unit 32 of fourth station 7 located behind first station 4. Heating section 23 is associated with first heating station 31 and heating section 30 is associated with second heating station 32. Spray unit 8 is shown as located above second station 5. Lid lifter 9 is located beside second station 5.

Figure 4:
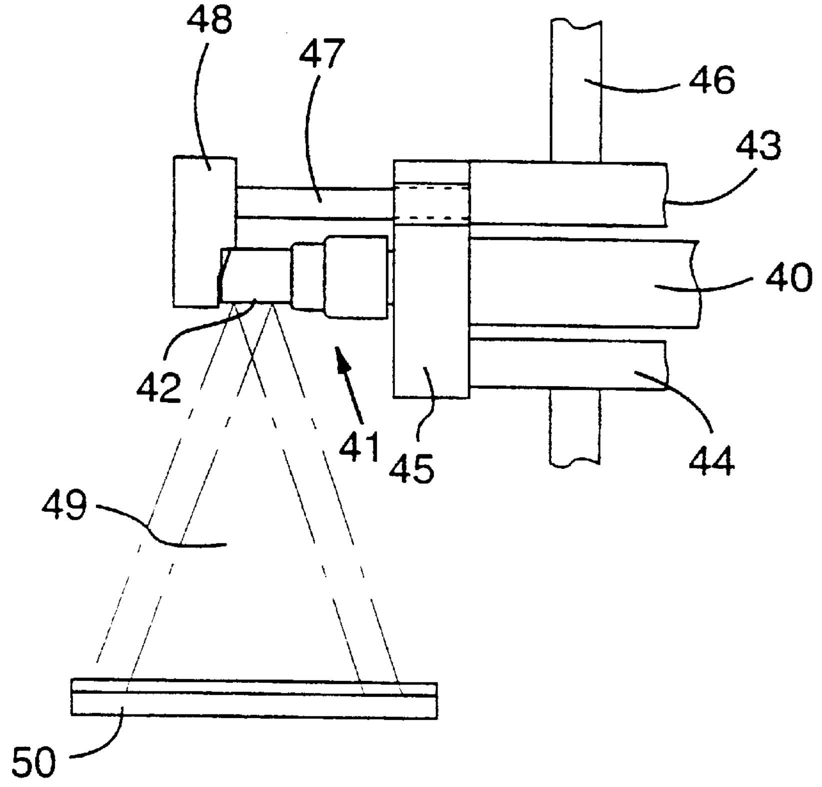
FIG. 4 is a schematic representation of a cross-section of a spray unit.

FIG. 4 shows a cross section of one embodiment of a spray unit, The spray unit shown in FIG. 4 has la spray canister 40 that is connected to a spray head 41, part of which is spray nozzle 42. Spray canister 40 is located between pistons 43 and 44 and held in place by spray holder 45, which is connected to pistons 43 and 44. Pistons 43 and 44 are mounted on spray mount 46. Piston rod 47 extends from spray holder 45 and terminates in piston plate 48. It will be noted that spray nozzle 42 abuts piston plate 48. Spray 49 extends from spray nozzle 42 to contact sample 50. It will be appreciated that a variety of spray units could be used, examples of which are illustrated in FIGS. 1 and 2 and in FIG. 4.

Figure 5:
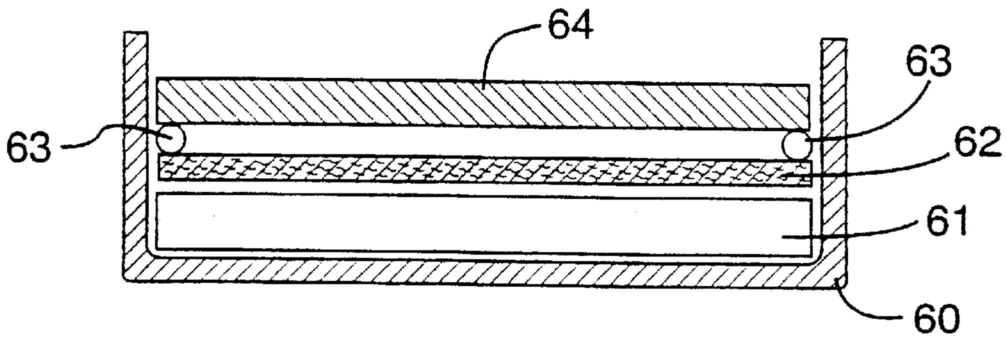
FIG. 5 is a schematic representation of a cross-section of a sample on a filter within a container.

FIG. 5 shows a cross section of a sample in a dish. The dish, 60, contains salt pad 61, which is optional, as discussed herein. Filter 62 lies on salt pad 61 and is held in placer and separated from cover 64 by spacer 63. Spacer 63 is conveniently in the form of an O-ring. It is to be noted that cover 64 could be in a variety of forms, including a cover insertable into a dish or onto a dish.

In use, a sample is placed on a suitable carrier for use in the apparatus. The carrier is most Preferably a filter, with the sample being placed on the filter by standard filtration techniques. For instance, if the particular material to be tested is a solution e.g. a water sample or other fluid, the filter could be placed in a standard flat-bottomed filtration funnel and the sample filtered to be retained on the filter. This would result in the cells of the particular species to be detected being scattered randomly on the filter, which would facilitate detection at a later stage. In alternative procedures, the sample could be on a membrane, a microscope slide or in a microtitre dish, or in some other suitable form. It is understood that the sample should be substantially planar and of a size that will fit within the dish that is used in the rotary thermocycling apparatus 1. It is understood that the dish referred to herein is any suitable flat bottomed receptacle that will fit within the stations of the apparatus and retain the sample, including cover plates, salt pads or any other item placed within the dish that is related to the reaction being conducted.

In order to conduct a poly erase chain reaction, the heating plates associated with the positions of the rotary thermocycling apparatus are heated to predetermined temperatures. For example, the first station could be at temperature of 50° C., the second station at the same temperature, third station at 72° C. and fourth station 96° C., it being understood that the temperatures are optimized for particular types of reactions. The sample is conveniently placed in the first station. If two samples are to be tested at the same time, the unit would be manually turned and the second sample placed in the station opposed to the first station. If four samples are to be tested, the unit would be manually rotated and samples placed in each of the stations.

The rotary thermocycling apparatus would preferably have automatic controls to control temperatures, as well as control other parameters relating to the process, particularly the dwell time at each station, the duration and timing of any spray that is used and the number of sequential steps in the reaction.

The sample is placed in the rotary table at the first station and then rotated to the second station. At the second station, lid lifter 9 rotates over the second station and lid lifter suction cap 13 is moved downwards to contact the cover plate on the sample. The suction cup 13 is then retracted and moved out of position, taking with it the cover, and thereby exposing the sample on the filter. Piston rod 47 of the spray unit (see FIG. 4) then retracts into piston 43, whereby piston plate 48 pushes on spray nozzle 42. This causes the spray to activate and liquid reagent(s) to be sprayed downwards onto the filter. The duration the spray may be any convenient length of time, typically 0–5–2 seconds, after which the procedure is reversed and the cover is replaced on the filter. At the appropriate cycle time, rotary table 3 rotates so that the sample be comes positioned at the third station. At this station, heating unit 31 descends onto the sample and into contact with the cover. The sample at this time is heated from below by the heated plate to a pre-determined temperature, for example 72° C., and simultaneously heated from above by the heating unlit to the same temperature. At the end of the cycle time, rotary table 3 rotates to position the sample at the fourth station, at which it is heated from below the heating plate at this station to a predetermined temperature, for example 96° C., and from above by heating unit 32 to the same temperature. It is understood that the temperatures would be optimized for the particular reaction.

The sample is then rotated back to the first station, and is cooled to 50° C., the pre-determined temperature at that station. It is preferred that as the rotary table 3 rotates the sample from the fourth station to the first station, that the rotary table also effect a turning of the sample e.g. by 25–50°. This may conveniently be obtained by means of a ratchet mechanism on the side of the rotary table 3 (not shown). The turning of the sample to change the orientation of the sample in rotary table 3 randomises any inconsistencies in, in particular, the spray unit, as, well as heating of the sample so that, after a number of cycles, all parts of the sample on the filter are treated to essentially the same conditions.

Accelerated cooling of the sample between the fourth station, which is at a temperature of for example 96° C., and the first station at a temperature of for example 50° C. may be desirable. Such accelerated cooling could involve use of refrigeration, air jets and/or fans between the fourth and first stations. A preferred method of cooling is use of a vortex tube, or a ranque vortex tube, to direct a stream of cooling air onto the sample. One example of a vortex tube is an EXAIR™ vortex from EXAIR Corporation of Cincinatti, Ohio, which is constructed of stainless steel.

The filter needs to be made from an inert material i.e. a material that is stable under the conditions of use, especially temperature, which does not affect the sample on the filter. A preferred filter is formed from nylon, with a pore size of 0.2 mm. If the disk that is used has a diameter of 92 mm, then the filter is conveniently of a diameter of 90 mm. The sample of bacteria, or other target, becomes trapped between the fibers of the filter (membrane).

Extraneous extracellular DNA would normally be removed from cells by incubation of the sample with nuclease solution applied in a fine spray. The nuclease would then be inactivated and denatured by heat.

Bacterial cells would normally be lysed by a treatment suitable for the expected species. This could include one or more of the following: temperature shock, enzymic digestion and application of a detergent. Removal of extracellular DNA and lysing of bacterial cells would normally take place prior to placing the sample in the rotary thermocycler apparatus.

It is preferred that the dish contain a pad of salt, particularly an 89 mm diameter glass-fibre filter disc that contains the solutes required for the PCR process. The spacer is conveniently a silicone rubber O-ring, having an external diameter of 92 mm. The cover is preferably an 89 mm Teflon™ fluoropolymer cover, in the form of a flat disc.

Reference is made herein to the use of covers on the samples, which are removed prior to spraying with reagent and then replaced. A wide variety of covers could be used, including discs as described herein and lids that fit over the sample container (dish). Preferred covers fit closely to but are spaced from samples e.g. by use of O-rings, but also permit heating units to be lowered into contact therewith for purposes of rapid and easy temperature adjustment and temperature control of the sample. All types of covers are generally referred to herein as cover plates but are to be understood to include discs and other types of covers.

In preferred embodiments of the invention, the spray unit is a small aerosol container or pump spray unit containing the liquid reagent(s) for the reaction. A small aerosol container of reagent(s) is convenient, as it enables the container to be readily replaced with another container of the same or different reagent(s). However other types of spray units may be used with the apparatus of the invention.

Although the present invention is particularly described herein with reference to use of one spray unit, more than one spray unit could be used at the same or different stations. For instance, a programmed sequence of at least two different sprays could be used. It is also understood that in some circumstances, the spray(s) could be used in other than each cycle of the apparatus. More than one liquid reagent may be used, either as a combination of reagents in one spray unit, or as reagents in separate spray units that are sprayed simultaneously, in sequence in the same cycle, in different cycles or in some other manner.

The apparatus has bees particularly described herein with respect to manual insertion and removal of the flat-bottom containers onto and from the first station. However, it is understood that flat-bottom containers could be automatically inserted onto and removed from the first station, to permit more efficient use of the apparatus and the ability of the apparatus to operate essentially unattended by an operator, including overnight, or for other reasons.

The apparatus has been described herein with a shaft 14, which could be used for support of heating units, spray units or the like. However, in a preferred embodiment (not shown), shaft 14 is omitted and other means are provided to support heating, spray and other units. Omission of shaft 14 permits rotating table 3 to be a removable table, to permit cleaning of the table and beneath the table and to permit replacement of the table with another table e.g. with stations of different sizes or shapes e.g. square or oval shapes, or to expedite adaption of the apparatus to a different number of stations.

After use of the rotary thermocycler apparatus, it is necessary to take steps to detect the reaction products on the filter. In one example of such steps, double-stranded DNA reaction products on the filter may be sprayed with SYBR™DX reagent from Molecular Probes, Inc. of Eugene, Oreg., USA., or another stain, specific for the double-stranded DNA. The stained clots of double-stranded DNA fluoresce as dots on a dark background under ultraviolet (UV) light. A photo Image may be captured by an electronic camera and quantitatively analyzed using computer software to give a cell count for the targeted bacteria in the original sample.

Single-stranded DNA reaction products are tested for hybridization with a single-stranded DNA sequence probe specific to the expected product. Such probes may be readily detected using radio active labels, or labels that induce photochemical reactions e.g. chemiluminescence, or by other methods. This test would allow for authenticity of the PCR product to be checked simultaneously with quantitative analysis.

It will be understood that a wide variety of steps could be taken to detect, identify and quantify reaction products on the filter or other medium used.

The original sample of bacterial cell suspension or other material received for testing will frequently be diluted prior to filtering the sample. Thus, the count obtained at the end of a test e.g. using fluorescence, will need to be adjusted to reflect any dilution.

In some circumstances, it may be desirable to conduct one or more preliminary steps in preparation a sample prior to conducting PCR or other tests in the apparatus of the invention. For instance, a sample of for example bacterial cells on a filter could be placed on growth medium agar and incubated. The cells would multiply, and the resultant micro colonies would be more readily detected using PCR in the apparatus described herein.

A mixed population of calls may be tested. In a mixed population, it is possible to detect one or more specific cell types containing the target DNA, so that the presence or absence of such cell types may be detected, while not detecting other cell types that do not contain the target DNA.

PCR specificity depends primarily on the choice of primers used to prime the target DNA synthesis and the stringency of the reaction conditions e.g. temperature of DNA annealing, concentration of reagents and other factors. This could enable the detection of a carrier of a particular gene, or solely those members of a taxonomic group that act as a carrier of a DNA sequence diagnostic for that up.

In use of the apparatus of the invention using a spray, DNA polymerase enzyme is sprayed on the sample during each cycle, or as otherwise programmed in the sequence of steps in the apparatus. Consequently, it may not be necessary to use a heat-stable enzyme that must be sufficiently stable to denaturation temperatures to be active during the entire PCR process. Even if the enzyme were to be fully or partially destroyed at the denaturation temperatures being used, it would be replaced in the next spray step. Thus, it might be beneficial to use a cheaper less heat-stable enzyme, and possibly more of such an enzyme, rather than a more expensive enzyme that would be stable at the denaturation temperatures used in each cycle. As an example, it might be possible to use Klenow enzyme in place of Taq DNA polymerase in a PCR process, with appropriate adjustment of the optimal temperature of use, and obtain acceptable results.

While the present invention has been particularly described herein with reference to PCR, other reactions could be carried out e.g. involving bacteria, DNA fragments in gel profile blots, viruses or the like, provided the samples could be obtained in a suitable from and appropriate occupational health precautions taken if necessary.

The heating units of stations 5 and 6 have an important effect on the rate at which the sample reaches the required temperature, by reducing the depth of space that has to be heated. Thus, the volume to be heated extends from the cover to the base of the dish, which is simultaneously being heated from below. In the present invention, that volume is small.

An important aspect of tie present invention is that the rate of cycling may be increased, because each station remains at its pre-selected temperature, and it is not necessary to change the temperature of a metal block frequently during each cycle.

The apparatus and method of the present invention may be used in a wide range of tests. Examples of such tests include detection of the presence of *E. coli*, Listeria and Salmonella, and other bacteria, using reagents known for use in detection of such bacteria. The apparatus and methods of the invention may also be used in other types of tests that require cycling of temperatures and spay of reagents. For instance, the apparatus and methods could be usable with some metallic catalyst reactions e.g. platinum catalysed reactions using hydrogen peroxide, other reactions that use thermocycling, formation of layered polymer structures in which thin layers e.g. of a thermosetting polymer, are polymerized in each cycle, and in detection techniques that require thermocycling.

What is claimed is:

1. A rotary thermocycling apparatus, especially for biochemical reactions, comprising:

(a) a plurality of stations for receiving samples in a flat-bottomed container, each station having a flat heated plate on which said container is placed and having means to independently control said heated plate at a pre-determined temperature;

(b) means to move each said flat-bottomed container from one station to another station in a pre-determined sequence;

(c) at least two of said stations having a heating unit adapted to be lowered over a container located on said station, each heating unit being comprised of a section with a flat lower surface that is adapted to be lowered into said container close to but not in contact with the sample in said container; and (d) at least one station, in addition to the stations of (c), having a spray unit adapted to spray a liquid reagent(s) into a container located at said one station.

2. The apparatus of claim 1 in which there are at least four stations.

3. The apparatus of claim 1 in which said station of (d) is adapted for removal of a cover plate from a container located on said station prior to activation of the spray, and for replacement of the cover plate after said spray has terminated.

4. The apparatus of claim 1 in which said stations of (a) are adapted to receive a flat-bottomed container of a dimension less than that of the station.

5. The apparatus of claim 3 in which said lower surface of the heating unit is adapted to be lowered into contact with a cover plate in the container.

6. The apparatus of claim 3 in which the apparatus has a programmer for controlling at least (i) the temperature at each station, (ii) the dwell time in each station, (iii) the duration and timing of the spray(s), and (iv) the number of sequential cycles for the biochemical reaction.

7. The apparatus of claim 6 in which the apparatus is programmable and automated.

8. The apparatus of claim 7 in which the apparatus is adapted to process more than one sample at a time, up to one for each station in the apparatus.

9. The apparatus of claim 7 in which there is an automatic loader for placing containers into the apparatus and for removing containers therefrom.

10. The apparatus of claim 3 in which the heating units are on pistons that are lowered into the containers.

11. The apparatus of claim 3 in which the station with the spray unit is followed in sequence by the two stations having heating units.

12. The apparatus of claim 1 in which the means to move each said flat-bottomed container from one station to another station in (b) is a rotatable table adapted to receive said flat-bottomed containers, said flat-bottomed containers when so received being movable in said pre-determined sequence from said one station to said another by rotation of said table.

13. A method for a sequential reaction especially a sequential biochemical reaction at different temperatures, comprising:

(a) placing a sample in a flat-bottomed container;

(b) sequentially cycling said sample through predetermined changes in temperature by placing said flat-bottomed container on flat heated plates at each said temperature for a predetermined period of time;

(c) spraying said sample with at least one liquid reagent;

(d) controlling (i) the temperature at each station, (ii) the dwell time in each station, (iii) the duration and timing of the spray(s), and (iv) the number of sequential cycles for the biochemical reaction, said controlling of the temperature is at at least two stations and includes the step of lowering a heating unit over the containers at said at least two stations, each heating unit being comprised of a section with a flat lower surface that is adapted to be lowered into said container close to but not in contact with the sample in said container.

14. The method of claim 13 in which the container has a cover plate, said cover plate being removed prior to step (c) and replaced thereafter.

15. The method of claim 13 in which the biochemical sample is located on a filter, a membrane, a microlitre container or microscope slide in said container.

16. The method of claim 13 in which the method is performed by a programmable and automated device.

17. The method of claim 13 in which the sample is subjected to a pre-treatment prior to the method for the sequential reaction.

18. The method of claim 15 in which a spacer is placed on the filter and a cover plate is placed on the spacer.

19. The method of claim 13 in which the reaction is a polymerase chain reaction.

20. The method of claim 13 in which the reaction is for detection of specific DNA sequences.

21. The method of claim 13 in which the reaction is for detection of bacteria.

22. The method of claim 13 in which the reaction is for enumeration of a distinct type of bacterium or species.

23. The method of claim 13 in which the sample is subjected to a photochemical detection process subsequent to the reaction to detect product of the reaction.

24. The method of claim 23 in which the photochemical detection process comprises fluorescence.

25. The method of claim 24 in which the electronic recording is made of the photochemical detection process.

26. The method of claim 25 in which the electronic recoding is made by using a video camera.

* * * * *

UNITED STATES PATENT AND TRADEMARK OFFICE

CERTIFICATE OF CORRECTION

PATENT NO. : 6,448,066 B1
DATED : September 10, 2002
INVENTOR(S) : Roger George Laurence Wheatcroft It is certified that error appears in the above-identified patent and that said Letters Patent is hereby corrected as shown below:

Column 1,
Line 8, before “especially” delete “apparatus” and insert therefor -- apparatuses --
Line 16, after “invention” delete “w 11” and insert therefor -- will --
Line 22, after “immediate” insert -- medical --
Line 24, after “be” delete “Able” and insert therefor -- able --
Line 34, after “in” delete “al” and insert therefor -- all --

Column 2,
Line 2, after “involves” delete “Denaturing” and insert therefor -- denaturing --
Line 14, after “templates” delete “or” and insert therefor -- for --
Line 56, after “controlled” delete “mariner” and insert therefor -- manner --

Column 3,
Line 15, after “of” (second occurrence) delete “t e” and insert therefor -- the --
Line 31, after “embodiment” delete “it,” and insert therefor -- , --

Column 5,
Line 31, after “supports” delete “128” and insert therefor -- 28 --
Line 48, after “21” delete “alone” and insert therefor -- along --
Line 62, after “unit” insert -- 8 --

Column 6,
Line 6, after “station” insert -- 6 --
Line 20, before “so” delete “112” and insert therefor -- 12 --
Line 36, after “unit” (first occurrence) delete “,” and insert therefor -- . --

UNITED STATES PATENT AND TRADEMARK OFFICE
CERTIFICATE OF CORRECTION

PATENT NO. : 6,448,066 B1 
DATED : September 10, 2002
INVENTOR(S) : Roger George Laurence Wheatcroft It is certified that error appears in the above-identified patent and that said Letters Patent is hereby corrected as shown below:

Column 6 (cont),
Line 36, after "has" delete "la" and insert therefor -- a --
Line 50, after "in" delete "placer" and insert therefor -- place --
Line 56, after "most" delete "Preferably" and insert therefor -- preferably --

Signed and Sealed this

Sixth Day of July, 2004

JON W. DUDAS
*Acting Director of the United States Patent and Trademark Office*